United States Patent [19]

Zeidler et al.

[11] 4,170,655
[45] Oct. 9, 1979

[54] STABLE AQUEOUS OR AQUEOUS-ALCOHOLIC SOLUTIONS OF FAT-SOLUBLE PERFUME OILS OR DRUGS CONTAINING HYDROXYALKYL ESTER- OR N-(HYDROXYALKYL) AMIDE-ETHOXYLATES

[75] Inventors: Ulrich Zeidler; Fanny Scheuermann, both of Düsseldorf, Fed. Rep. of Germany

[73] Assignee: Henkel Kommanditgesellschaft auf Aktien, Dusseldorf-Holthausen, Fed. Rep. of Germany

[21] Appl. No.: 826,044

[22] Filed: Aug. 19, 1977

[30] Foreign Application Priority Data

Sep. 1, 1976 [DE] Fed. Rep. of Germany ....... 2639293

[51] Int. Cl.$^2$ .................. A61K 31/16; A61K 31/20; A61K 31/25; A61K 31/355
[52] U.S. Cl. .................................... 424/284; 424/307; 424/318; 424/320; 424/344; 252/522
[58] Field of Search .................. 424/284, 307; 252/522

[56] References Cited

U.S. PATENT DOCUMENTS 3,102,114  8/1963  Komori et al. ...................... 424/284

FOREIGN PATENT DOCUMENTS 2019839 11/1970 Fed. Rep. of Germany ........... 424/284
1077723  8/1967 United Kingdom ..................... 424/307
1236703  6/1971 United Kingdom .

OTHER PUBLICATIONS

Am. Hosp. Formulary Service, vol. 2 (1965) pp. 88:4; and 88:16.
Surface Actice Agent, vol. 1, Schwartz & Perry (1949) pp. 510–513.
McCutheon's–Detergents & Emulsifiers (1971) Allured Publ. Corp., pp. 23, 39, 43 and 164.

*Primary Examiner*—Albert T. Meyers
*Assistant Examiner*—D. W. Robinson
*Attorney, Agent, or Firm*—Hammond & Littell

[57] ABSTRACT

Stable, aqueous or aqueous-alcoholic solutions of fat-soluble perfume oils or drugs, containing hydroxyalkyl ester- and/or N-(hydroxyalkyl)-amide-ethoxylates of the formula

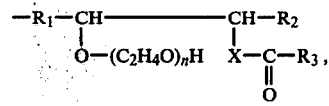

wherein $R_1$ and/or $R_2$ are an alkyl group having 1 to 18 carbon atoms or hydrogen, $R_3$ is an alkyl group having 1 to 12 carbon atoms or an aryl group, X is an oxygen atom, the group >NH or the group >N—$(C_2H_4O)_m$H, and n and m are integers of from 0 to 40, with the proviso that the total of the carbon atoms of $R_1+R_2$ is from 6 to 20 and the total of the numbers n+m is a value from 6 to 40.

8 Claims, No Drawings

STABLE AQUEOUS OR AQUEOUS-ALCOHOLIC SOLUTIONS OF FAT-SOLUBLE PERFUME OILS OR DRUGS CONTAINING HYDROXYALKYL ESTER- OR N-(HYDROXYALKYL) AMIDE-ETHOXYLATES

RELATED ART

Water-soluble perfume oils can be used in many cases for the purpose of perfuming clear, aqueous or low concentration alcoholic cosmetics such as face lotions, after-shave lotions and hair lotions. However, the majority of ethereal perfumes, perfume oils and fragrances are oil-soluble products which can be converted to clear, stable aqueous or aqueous-alcoholic solutions only by the addition of so-called dissolving intermediaries. It is already known to solubilize oil-soluble products by using various dissolving intermediaries such as mono fatty acid esters of polyols such as sorbitol monostearate or various ethylene oxide addition compounds such as polyethoxylated castor oil. A substantial disadvantage of the dissolving intermediaries used up until now is that relatively large quantities have to be added in order to convert the desired and required quantities of perfume oils or drugs to a stable, aqueous or low concentration alcoholic solution. A further disadvantage is that their action as a dissolving intermediary is generally very specific and extends only to a limited number of perfume oils or drugs.

Therefore, there is a need to develop dissolving intermediaries which, even when added in small quantities, make it possible to prepare clear, stable, aqueous or low concentration alcoholic solutions containing the required concentration of various perfume oils and drugs.

OBJECTS OF THE INVENTION

An object of the present invention is the development of an intermediary which, even in low concentration, can act as a solubilizing agent in the preparation of clear, stable, aqueous or aqueous-alcoholic solutions containing effective concentrations of a great many fat-soluble perfume oils or drugs.

Another object of the present invention is the production of a clear, stable, aqueous or aqueous-alcoholic solution of a fat-soluble perfume oil or drug, which contains hydroxyalkyl ester- and/or N-(hydroxyalkyl)-amide-ethoxylates of the formula

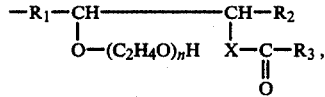

wherein $R_1$ and/or $R_2$ are an alkyl group having 1 to 18 carbon atoms or hydrogen, $R_3$ is an alkyl group having 1 to 12 carbon atoms or an aryl group, X is an oxygen atom, the group >NH or the group >N—$(C_2H_4O)_mH$, and n and m are integers of from 0 to 40, with the proviso that the total of the carbon atoms of $R_1+R_2$ is from 6 to 20 and the total of the numbers $n+m$ is a value from 6 to 40.

A still further object of the present invention is the development of an improved process for solubilizing oil- or fat-soluble substances in stable, aqueous or aqueous-alcoholic solutions by using as dissolving intermediaries hydroxyalkyl ester- and N-(hydroxyalkyl) amide-ethoxylates of the formula

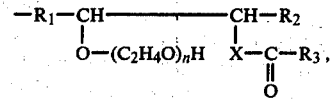

wherein $R_1$ and/or $R_2$ are an alkyl group having 1 to 18 carbon atoms or hydrogen, $R_3$ is an alkyl group having 1 to 12 carbon atoms or an aryl group, X is an oxygen atom, the group >NH or the group >N—$(C_2H_4O)_mH$, and n and m are integers of from 0 to 40, with the proviso that the total of the carbon atoms of $R_1+R_2$ is from 6 to 20 and the total of the numbers $n+m$ is a value from 6 to 40.

These and other objects of the invention will become more apparent as the description thereof proceeds.

DESCRIPTION OF THE INVENTION

It has now been found that the above objects can be achieved by employing hydroxyalkyl ester- or N-(hydroxyalkyl) amide-ethoxylates as dissolving intermediaries to form stable, aqueous or aqueous-alcoholic solutions of fat-soluble substances, especially perfume oils or drugs.

The present invention relates to clear, stable, aqueous or aqueous-alcoholic solutions of fat-soluble substances, especially perfume oils or drugs, which contain an effective amount of hydroxyalkyl ester- and/or N-(hydroxyalkyl amide-ethoxylate dissolving intermediaries of the formula

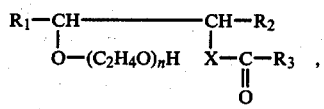

wherein $R_1$ and $R_2$ independently of each other are a member selected from the group consisting of alkyl having 1 to 18 carbon atoms and hydrogen, $R_3$ is a member selected from the group consisting of alkyl having 1 to 12, preferably 1 to 5, carbon atoms, and aryl, preferably phenyl, X is a member selected from the group consisting of oxygen, >NH and >N—$(C_2H_4O)_mH$, and n and m independently of each other are an integer from 0 to 40, with the proviso that the total of the carbon atoms of $R_1+R_2$ is from 6 to 20 and the total of $n+m$ is from 6 to 40.

More particularly, the present invention is directed to a stable, aqueous or aqueous-alcoholic solution comprising (1) from 0.1% to 1% by weight, relative to the total weight of the solution, of a fatty substance, preferably a perfume oil or drug, (2) from 0.1% to 20%, preferably 0.5% to 5%, by weight, relative to the total weight of the solution, of hydroxyalkyl ester- and/or N-(hydroxyalkyl) amide-ethoxylates of the formula

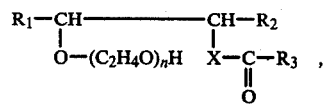

wherein $R_1$ and/or $R_2$ are an alkyl group having 1 to 18 carbon atoms or hydrogen, $R_3$ is an alkyl group having 1 to 12 carbon atoms or an aryl group, X is an oxygen atom, the group >NH or the group >N—$(C_2H_4O)_mH$, and n and m are integers of from 0 to 40, with the proviso that the total of the carbon atoms of $R_1+R_2$ is from 6 to 20 and the total of the numbers $n+m$ is a value from 6 to 40, and (3) the remainder to 100% by weight of the conventional substances, including the water or water-/alcohol solvent, used in said solutions.

The dissolving intermediary of the invention can thus be (1) a hydroxyalkyl ester- ethoxylate of the formula $$R_1-CH-CH-R_2$$
$$\phantom{R_1-CH}|\phantom{-CH-}|$$
$$O-(C_2H_4O)_nH \quad X-C-R_3,$$
$$\phantom{O-(C_2H_4O)_nH \quad X-}\|$$
$$\phantom{O-(C_2H_4O)_nH \quad X-}O$$

wherein $R_1$ and $R_2$ independently are alkyl of 1 to 18 carbon atoms or hydrogen, $R_3$ is alkyl of 1 to 12, preferably 1 to 5, carbon atoms or aryl and n is an integer from 6 to 40, with the proviso that the total carbon atoms of $R_1+R_2$ is from 6 to 20, or a mixture of said hydroxyalkyl ester-ethoxylates.

(2) an N-(hydroxyalkyl)-amide-ethoxylate of the formula $$R_1-CH-CH-R_2$$
$$\phantom{R_1-}|\phantom{-CH-}|$$
$$O-(C_2H_4O)_nH \quad Z-C-R_3,$$
$$\phantom{O-(C_2H_4O)_nH \quad Z-}\|$$
$$\phantom{O-(C_2H_4O)_nH \quad Z-}O$$

wherein $R_1$ and $R_2$ independently are alkyl of 1 to 18 carbon atoms or hydrogen, $R_3$ is alkyl of 1 to 12, preferably 1 to 5, carbon atoms or aryl, Z is the group $>N-H$ or the group $>N-(C_2H_4O)_mH$, and n and m are integers from 0 to 40, with the provisos that the total carbon atoms of $R_1+R_2$ is from 6 to 20, and that the total of $n+m$ is from 6 to 40, or a mixture of said N-(hydroxyalkyl)-amide-ethoxylates; or (3) a mixture of the above hydroxyalkyl ester- and N-(hydroxyalkyl)-amide-ethoxylates.

The preparation of the hydroxyalkyl ester- and N-(hydroxyalkyl)amide-ethoxylates to be used in the solutions of the invention can be effected in known manner. For example, they can be produced in a known manner in a two-stage synthesis by reacting an epoxyalkane of the formula $$R_1-CH-CH-R_2$$
$$\phantom{R_1-CH}\diagdown\phantom{-}\diagup$$
$$\phantom{R_1-CH--}O$$

with a carboxylic acid of the formula $$R_3-C-O-H$$
$$\phantom{R_3-}\|$$
$$\phantom{R_3-}O$$

or a carboxylic acid amide of the formula $$R_3-C-NH_2$$
$$\phantom{R_3-}\|$$
$$\phantom{R_3-}O$$

to form an adduct of the formula $$R_1-CH-CH-R_2 \qquad R_1-CH-CH-R_2$$
$$\phantom{R_1-}|\phantom{CH-}|\phantom{-R_2 \qquad R_1-}|\phantom{CH-}|$$
$$OH \quad O-C-R_3 \quad or \quad OH \quad HN-C-R_3 \; ,$$
$$\phantom{OH \quad }\|\phantom{-C-R_3 \quad or \quad OH \quad HN-}\|$$
$$\phantom{OH \quad }O\phantom{-C-R_3 \quad or \quad OH \quad HN-}O$$

wherein $R_1$, $R_2$, and $R_3$ are as defined above, and by ethoxylation of said adduct. This method of production is primarily recommended when terminal epoxides are used as starting material in the above synthesis.

Moreover, the hydroxyalkyl amide-ethoxylates can also be obtained in a known manner by adding the nitrile $R_3-CN$ to an epoxyalkane of the formula $$R_1-CH-CH-R_2$$
$$\phantom{R_1-CH}\diagdown\phantom{-}\diagup$$
$$\phantom{R_1-CH--}O$$

with subsequent saponification to form the amide, and subsequent ethoxylation. This method is particularly suitable when non-terminal epoxyalkanes are used as starting materials.

In a further method of production, an epoxyalkane of the formula $$R_1-CH-CH-R_2$$
$$\phantom{R_1-CH}\diagdown\phantom{-}\diagup$$
$$\phantom{R_1-CH--}O$$

is reacted with ammonia to form the corresponding vicinal hydroxyalkylamine $$R_1-CH-CH-R_2$$
$$\phantom{R_1-}|\phantom{CH-}|$$
$$OH \quad NH_2$$

This product is then acylated with a corresponding acid halide, e.g.

$$R_3-COCl,$$

to form the amide $$R_1-CH-CH-R_2$$
$$\phantom{R_1-}|\phantom{CH-}|$$
$$OH \quad NH-CO-R_3$$

which is subsequently ethoxylated to form, in a known manner, the N-(hydroxyalkyl)amide ethoxylate.

Terminal epoxyalkanes which are particularly suitable as starting materials for producing the hydroxyalkyl ester- and hydroxyalkyl amide- ethoxylates are those having chain lengths in the range $C_{12}-C_{18}$. Preferred non-terminal epoxyalkanes acting as starting materials are derived from monoolefins having chain lengths in the range $C_{11}-C_{14}$ and from monoolefins having chain lengths in the range $C_{15}-C_{18}$. These monoolefins have the following chain length distributions:

$C_{11}-C_{14}$ olefins:
  $C_{11}$ olefins, approximately 22 percent by weight,
  $C_{12}$ olefins, approximately 30 percent by weight,
  $C_{13}$ olefins, approximately 26 percent by weight,
  $C_{14}$ olefins, approximately 22 percent by weight.
$C_{15}-C_{18}$ olefins:
  $C_{15}$ olefins, approximately 26 percent by weight,
  $C_{16}$ olefins, approximately 35 percent by weight,
  $C_{17}$ olefins, approximately 32 percent by weight,
  $C_{18}$ olefins, approximately 7 percent by weight.

A variety of commercially available mixtures of monoolefins are available as starting materials for the preparation of the above-mentioned epoxyalkanes.

Suitable mixtures of monoolefins can be obtained by dehydrogenation (catalytically or by chlorination followed by dehydrochlorination) of linear paraffins of 11 to 20 carbon atoms followed by removal of the monoolefin content of the reaction product (by distillation or selective extraction, as may be preferred). In the monoolefins the double bonds are substantially non-terminal and are distributed statistically along the "backbone"

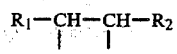

chain. Various fractions are obtainable from these monoolefin mixtures, of which the two above-mentioned $C_{11}-C_{14}$ and $C_{15}-C_{18}$ olefin fractions are particularly suitable for use in the present invention.

On the other hand, it is also possible to use olefin mixtures which are prepared by aluminochemical methods and which have unbranched alkyl chains with 12 to 20 carbon atoms. These mixtures have a high (i.e., more than 50%) proportion of terminal unsaturation. Examples of suitable commercial products are those having the chain length distributions shown below:

| Olefin Fractions Used | |
|---|---|
| Fraction | % by Wt. |
| (c) $C_{12}-C_{14}$ - fraction | |
| $C_{12}$ Terminal | 55 |
| $C_{14}$ Terminal | 31 |
| $C_{12}$ Non-Term. | 5 |
| $C_{14}$ Non-Term. | 8 |
| (d) $C_{14}-C_{16}$ fraction | |
| $C_{14}$ Terminal | 53 |
| $C_{16}$ Terminal | 28 |
| $C_{14}$ Non-Term. | 7 |
| $C_{16}$ Non-Term. | 11 |
| (e) $C_{16}-C_{18}$ fraction | |
| $C_{16}$ Terminal | 35 |
| $C_{18}$ Terminal | 23 |
| $C_{20}$ Terminal | 2 |
| $C_{16}$ Non-Term. | 11 |
| $C_{18}$ Non-Term. | 21 |
| $C_{20}$ Non-Term. | 5 |

But it is also possible to use olefin mixtures which contain saturated hydrocarbons when they are obtained with the olefin mixtures.

By means of known methods, e.g. reaction with peracids like peracetic acid, there are obtained the epoxyalkane mixtures from which the hydroxyalkyl ester- and hydroxyalkyl amide-ethoxylates of the present invention can be obtained.

Particularly suitable dissolving intermediaries for use in the clear, stable, aqueous or aqueous-alcoholic solutions of fat-soluble perfume oils or drugs of the invention are those hydroxyalkyl ester- and N-(hydroxyalkyl)-amide-ethoxylates which are derived from mixtures of olefins. Among such dissolving intermediaries, those are particularly important in which the ester- or amide grouping is derived from acetic acid or acetamide. The preferred number of ethylene oxide (EO) groups to be added in the formation of the hydroxyalkyl ester- and N-(hydroxyalkyl)-amide-ethoxylates is from 10 to 30. An especially valuable group of dissolving intermediaries of the invention are those which are derived from terminal $C_{16}-C_{18}$ epoxyalkanes, preferably those hydoxyalkyl ester- and N-(hydoxyalkyl)-amide ethoxylates wherein the ester- or amide grouping is derived from acetic acid or acetamide, respectively, and the number of ethylene oxide (EO) groups added in the ethoxylation is from 10 to 30.

Among the preferred hydroxyalkyl ester- and N-(hydroxyalkyl)-amide-ethoxylates of the invention may be mentioned 2-hydroxy-$C_{16/18}$-alkyl acetate+15 EO, 2-hydroxy-$C_{16/18}$-alkyl acetate+30 EO, N-(2-hydroxy-$C_{16/18}$-alkyl) acetamide+10 EO, and N-(2-hydroxy-$C_{16/18}$-alkyl)acetamide+15 EO.

Among the suitable fat-soluble perfume oils which can be present in the solutions of the invention are natural or synthetic ethereal oils of all types, such as orange oil, pine oil, peppermint oil, eucalyptus oil, oil of lemons, carnation petal oil, cedar wood oil, bergamot oil, rosemary oil, patchouli oil, lavandine oil, spike oil, rose oil, vetiver oil, fennel oil, aniseed oil, thyme oil, geranium oil, lavender oil, menthol, as well as synthetic, oil-soluble perfume oils from the group of the aldehydes, esters and polyene compounds. By way of example, vitamin A, vitamin E and vitamin F (oil-soluble) may be mentioned as fat-soluble drugs.

The ratios of the quantity of fat-soluble perfume oil or fat-soluble medicinal substance to the quantity of hydroxyalkyl ester- or N-(hydroxyalkyl)amide-ethoxylate in the clear, stable, aqueous or aqueous-alcoholic solutions in accordance with the invention can vary within wide limits and depend upon the type of perfume oil or medicinal substance, the type of dissolving intermediary, the alcohol content and the other accompanying conventional substances which are present in the solution. The hydroxyalkyl ester- or N-(hydroxyalkyl)amide-ethoxylates can be present in quantities of from 0.1 to 20 percent by weight in the solutions in accordance with the invention, although they will generally be present in quantities of from 0.5 to 5 percent by weight, based on the total weight of the solution. As a general rule, the desired or required quantities of perfume oil or drug are not substantially in excess of or below the limits of from 0.1 to 1 percent by weight, relative to the total weight of the solution. Adjustment of the quantities of dissolving intermediary and fat-soluble perfume oil or drug, as needed to provide a clear, stable aqueous or aqueous-alcoholic solution, can be readily accomplished by those skilled in the art. The aqueous or aqueous-alcoholic, solutions of the invention can also contain, in addition to the dissolving intermediary and perfume oil or drug, conventional quantities of all the customary constituents used in such products.

The clear, stable, aqueous or aqueous-alcoholic solutions of fat-soluble perfume oils or drugs in accordance with the invention can be produced in a manner known per se by adding water or an alcohol-water mixture in the desired quantity ratio to concentrates of perfume oil or drugs and hydroxyalkyl ester- or N-(hydroxyalkyl)amide-ethoxylate. The appropriate quantity of water or of water and alcohol for the solutions of the invention can be readily determined by one skilled in the art. Suitable alcohols for use in said solutions are the water-miscible alcohols such as methanol, ethanol and isopropanol. An amount of water or of water and alcohol in the range from about 70–99 weight percent, relative to the total weight of the solution, serves as an example of the amount which might be present in the aqueous or aqueous-alcoholic solutions of the invention.

The solubilizing activity of the hydroxyalkyl ester- and N-(hydroxyalkyl) amide-ethoxylates of the invention is most evident in purely aqueous solutions or in aqueous solutions containing a low concentration of alcohol, such as e.g., under 10% by weight. Those aqueous-alcoholic solutions wherein the alcoholic content is from about 1 to 10% by weight of the total solution represent a particularly important embodiment of the invention. However, the alcoholic content of the aqueous-alcohol solutions of the invention can naturally vary over very wide limits, e.g. from only about 1% to 90% or over. The amount of alcohol to be used in the aqueous-alcoholic solutions of the invention will depend on various factors, including the nature of the fat-soluble substance being dissolved and of the dissolving intermediary being used and the intended application of the solutions.

The invention also includes a process of solubilizing a fat-soluble substance, especially a perfume oil or drug, in a clear, stable, aqueous or aqueous-alcoholic solution by means of a hydroxyalkyl ester- and/or N-(hydroxyalkyl) amide-ethoxylate of the formula

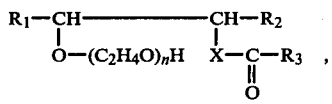

wherein $R_1$ and $R_2$ independently of each other are a member selected from the group consisting of alkyl having 1 to 18 carbon atoms and hydrogen, $R_3$ is a member selected from the group consisting of alkyl having 1 to 12, preferably 1 to 5, carbon atoms, and aryl, preferably phenyl, X is a member selected from the group consisting of oxygen, >NH and >N—($C_2H_4O)_m$H, and n and m independently of each other are an integer from 0 to 40, with the proviso that the total of the carbon atoms of $R_1+R_2$ is from 6 to 20 and the total of n+m is from 6 to 40.

The present invention will now be further described by means of the following Examples which are not to be limitative in any manner.

EXAMPLES

The production of the ethoxylates, to be used in accordance with the invention, will be described in the first instance. In the following examples, a 1,2-epoxy-$C_{16/18}$-alkane was used in the preparation of the dissolving intermediaries of the invention. The $C_{16}$–$C_{18}$ olefin mixture which was epoxidized to produce the above $C_{16}$–$C_{18}$ olefin epoxide mixture had the following chain length distribution:

| $C_{16}$–$C_{18}$ Olefins | (distribution in % by weight) |
|---|---|
| $C_{16}$ Terminal | (35) |
| $C_{18}$ Terminal | (23) |
| $C_{20}$ Terminal | (2) |
| $C_{16}$ Non-Terminal | (11) |
| $C_{18}$ Non-Terminal | (21) |
| $C_{20}$ Non-Terminal | (5) |

EXAMPLE 1

(A) 2-Hydroxy-$C_{16/18}$-alkyl acetate+30 moles of ethylene oxide(EO)

1 mole of a 1,2-epoxy-$C_{16/18}$-alkane and 1 mole of acetic acid were heated for 5 hours at 150° C. under agitation in the presence of 3 mole % of sodium acetate, relative to the epoxide. Any acetic acid still present was subsequently removed by distillation in vacuo. The hydroxyalkyl acetic acid ester produced was reacted in a conventional manner with 30 moles of ethylene oxide in an autoclave in the presence of sodium methylate acting as a catalyst. The hydroxy-$C_{16/18}$-alkyl acetate+30 EO obtained constitutes a yellowish pasty composition. The turbidity point measured for the 1% aqueous solution is 96° C.

(B) 2-Hydroxy-$C_{16/18}$-alkyl acetate+15 moles of ethylene oxide

The product 2-hydroxy-$C_{16/18}$-alkyl acetate+15 moles of ethylene oxide was produced in a fully analogous manner to that set forth above. The slightly yellowish, highly viscous composition has a turbidity point of 63° C. in 1% aqueous solution.

EXAMPLE 2

(A) N-(2-hydroxy-$C_{16-18}$-alkyl)acetamide+10 moles of ethylene oxide(EO)

1 mole of a 1,2-epoxy-$C_{16/18}$-alkane and 2 moles of acetamide were heated for 5 hours at 160° C. under agitation in the presence of 3 mole % of sodium methylate, relative to the epoxide. Finally, the reaction product was then washed with water to remove the surplus acetamide, and was dried. The N-(2-hydroxyalkyl)-acetamide produced was reacted in a conventional manner with 10 moles of ethylene oxide in an autoclave in the presence of sodium methylate acting as a catalyst. The N-(2-hydroxy-$C_{16/18}$-alkyl)acetamide+10 EO thus produced constitutes a slightly yellowish, viscous liquid. The turbidity point measured for the 1% aqueous solution is 79.5° C.

(B) N-(2-hydroxy-$C_{16/18}$-alkyl)acetamide+15 ethylene oxide

The product N-(2-hydroxy-$C_{16/18}$-alkyl)acetamide+15 ethylene oxide was produced in an analogous manner to that set forth above. The slightly yellowish, viscous liquid has a turbidity point of approximately 100° C. in 1% aqueous solution.

EXAMPLE 3

The following experiments were carried out in order to test the properties of the ethoxylates of the invention as dissolving intermediaries. A 1% aqueous solution of the perfume oil was prepared in each case. For this purpose, the perfume oil was in the first instance agitated together with the respective dissolving intermediary in a specific weight ratio, and sufficient water was subsequently added to produce a 1% solution relative to perfume oil. The ratios of dissolving intermediary:perfume oil chosen were 7:3 and 8:2, corresponding approximately to a 2-fold to 4-fold quantity of dissolving intermediary relative to perfume oil.

The following substances acted as dissolving intermediaries in the experiments:

L 1 2-hydroxy-$C_{16/18}$-alkyl acetate+15 EO
L 2 2-hydroxy-$C_{16/18}$-alkyl acetate+30 EO
L 3 N-(2-hydroxy-$C_{16/18}$-alkyl)acetamide+10 EO
L 4 N-(2-hydroxy-$C_{16/18}$-alkyl)acetamide+15 EO
L 5 Castor oil+40 EO (comparison substance).

The following 10 ethereal oils of differing composition and polarity acted as the test perfume oil substances in the experiments:

| | |
|---|---|
| 01 Rosemary oil | 06 Orange oil |
| 02 Bergamot oil | 07 Pine oil |
| 03 Cedar wood oil | 08 Peppermint oil |
| 04 Carnation petal oil | 09 Patchouli oil |
| 05 Oil of lemons | 010 Lavandine oil |

The properties of the individual aqueous solutions are given in the following Table, wherein x=turbid solution, xx=slightly turbid solution and xxx=clear, stable solution. Furthermore, the Table shows how many different oils a dissolving intermediary is able to dissolve. The larger the number of oils which a dissolving intermediary can dissolve, the higher is its value as a dissolving intermediary in general, since it can be used more universally. Naturally, the results given in the Table can be improved by a higher ratio of dissolving intermediary:perfume oil (DI:oil).

TABLE

| Dissolving intermediary | Ratio DI : oil | Oil | | | | | | | | | | Number of oils dissolved |
|---|---|---|---|---|---|---|---|---|---|---|---|---|
| | | 01 | 02 | 03 | 04 | 05 | 06 | 07 | 08 | 09 | 010 | |
| L 1 | 7:3 | X | X | X | X | X | X | X | X | X | X | |
| | | | | | | | | | | | | 5 |
| | 8:2 | XX | X | XXX | | X | XXX | XXX | XXX | X | XXX | X | |
| L 2 | 7:3 | X | X | X | X | X | X | X | X | X | X | |
| | | | | | | | | | | | | 2 |
| | 8:2 | XXX | X | | X | XXX | | X | XX | X | X | X | X | |
| L 3 | 7:3 | X | X | X | X | X | X | X | X | X | X | |
| | | | | | | | | | | | | 10 |
| | 8:2 | XXX | XXX | XXX | XXX | XXX | XXX | XXX | XXX | XXX | XXX | |
| L 4 | 7:3 | X | X | X | X | X | X | X | X | X | X | |
| | | | | | | | | | | | | 6 |
| | 8:2 | XXX | XXX | | X | XXX | XXX | XXX | XXX | X | X | X | |
| L 5 | 7:3 | X | X | X | X | X | X | X | X | X | X | |
| | | | | | | | | | | | | 0 |
| | 8:2 | XX | XX | XX | XX | XX | XX | X | XX | XX | XX | |

Experiments carried out in a corresponding manner with the fat-soluble vitamins A, E and F (oil soluble) showed that 0.5% clear aqueous solutions, relative to fat-soluble vitamin, can be produced when N-(2-hydroxy-$C_{16/18}$-alkyl) acetamide + 10 EO is used as a dissolving intermediary in a weight ratio of 3:1, relative to the vitamin.

In order to produce a clear aqueous-alcoholic solution having the same quantity of fat-soluble perfume oil as a purely aqueous solution, the quantities of dissolving intermediary required can be decreased as the alcohol content of the solution increases. Thus, a ratio of N-(2-hydroxy-$C_{16/18}$-alkyl)acetamide + 10 EO:perfume oil of 2:1 is sufficient in order to obtain clear 1% solutions of oil of lemons, orange oil, patchouli oil, bergamot oil in a mixture containing 60% of ethanol and 40% of water.

We claim:

1. Clear, stable, aqueous or aqueous-alcoholic solutions of a fat-soluble ethereal perfume oil or vitamin, consisting essentially of from 0.5% to 5% by weight, relative to the total weight of the solution, of a hydroxyalkyl ester-ethoxylate intermediary of the formula

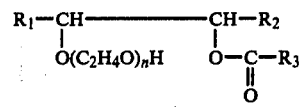

wherein $R_1$ and $R_2$ independently of each other are a member selected from the group consisting of alkyl having 1 to 18 carbon atoms and hydrogen, $R_3$ is a member selected from the group consisting of alkyl having 1 to 5 carbon atoms and phenyl, and n is an integer from 6 to 40 with the proviso that the total of the carbon atoms of $R_1+R_2$ is from 6 to 20, from 0.1% to 1% by weight relative to the total weight of the solution of a fat-soluble ethereal perfume oil or fat-soluble vitamin, wherein the amount of said ester-ethoxylate intermediary is at least four times the amount of said perfume oil or vitamin, from 0 to 10% by weight of a water-miscible alcohol, and the remainder to 100% by weight of the conventional substances used in said solution including water where the amount of water or water and alcohol is from 70% to 99% by weight, relative to the total weight of the solution.

2. The solution of claim 1, wherein $R_3$ is a methyl group.

3. The solution of claim 1, wherein n is an integer from 10 to 30.

4. The solution of claim 1, wherein one of $R_1$ or $R_2$ is hydrogen.

5. The solution of claim 4, wherein $R_3$ is a methyl group and n is an integer from 10 to 30.

6. The solution of claim 1 wherein the intermediary is a member selected from the group consisting of 2-hydroxy-$C_{16/18}$-alkyl acetate + 15 EO, and 2-hydroxy-$C_{16/18}$-alkyl acetate + 30 EO.

7. The solution of claim 1 wherein the fat-soluble vitamin is a vitamin selected from the group consisting of vitamin A, vitamin E and vitamin F.

8. The solution of claim 1 wherein the alcohol is a member selected from the group consisting of methanol, ethanol, isopropanol, and mixtures thereof.

* * * * *